United States Patent [19]
Gohbara et al.

[11] Patent Number: 6,143,312
[45] Date of Patent: Nov. 7, 2000

[54] WATERBORNE MICROBIAL PESTICIDES

[75] Inventors: Masatoshi Gohbara; Hiroshi Tsukamoto, both of Kanagawa, Japan

[73] Assignee: Japan Tobacco Inc., Tokyo, Japan

[21] Appl. No.: 09/125,746

[22] PCT Filed: Dec. 24, 1997

[86] PCT No.: PCT/JP97/04800

§ 371 Date: Aug. 25, 1998

§ 102(e) Date: Aug. 25, 1998

[87] PCT Pub. No.: WO98/28977

PCT Pub. Date: Jul. 9, 1998

[30] Foreign Application Priority Data

Dec. 25, 1996 [JP] Japan ................................. 8-345127

[51] Int. Cl.[7] ..................... A01N 25/34; A01N 63/00
[52] U.S. Cl. ..................... 424/408; 424/93.1; 424/405; 424/417; 424/421; 424/489; 424/490
[58] Field of Search ..................... 424/93.1, 405, 424/408, 417, 421, 489, 490

[56] References Cited

U.S. PATENT DOCUMENTS

| | | | |
|---|---|---|---|
| 5,273,749 | 12/1993 | Bok et al. ................................ | 424/405 |
| 5,283,060 | 2/1994 | Shieh ..................................... | 424/418 |
| 5,833,733 | 11/1998 | Wada et al. .............................. | 71/27 |

FOREIGN PATENT DOCUMENTS

| | | |
|---|---|---|
| 06321721 | 11/1994 | Japan . |
| 08040816 | 2/1996 | Japan . |
| 09140373 | 6/1997 | Japan . |

OTHER PUBLICATIONS

Kenney, *Weed Science*, vol. 34 (Suppl 1), pp.15–16 (1986).
Walker, *Weed Science*, vol. 29, Issue 3, pp.342–345 (1981).
Connick et al., *Weed Technology*, vol. 5, pp.442–444 (1991).
Egley et al., *Weed Technology*, vol. 7, pp.417–424 (1993).
Bryson et al., *Weed Technology*, vol. 4, pp.907–909 (1990).
Scheepens, *Weed Research*, vol. 27, pp.43–47 (1987).
Auld, *Crop Protection*, vol. 12, No. 6, pp.477–479 (1993).
Kloepper et al., *Phytopathology*, vol. 71, No. 6, pp.590–592 (1981).
Amsellem et al., *Phytopathology*, vol. 80, No. 10, pp.925–929 (1990).
Womack et al., *Biological Control*, vol. 6, pp.23–28 (1996).
Connick et al., *Biological Control*, vol. 1, pp.281–287 (1991).

*Primary Examiner*—Robert Harrison
*Attorney, Agent, or Firm*—Birch, Stewart, Kolasch & Birch, LLP

[57] ABSTRACT

Disclosed is a water-floating microbial pesticide comprising a microorganism, a water-in-oil type surfactant, oil, and powder having a low bulk specific gravity. Also disclosed are a method for producing the water-floating microbial pesticide and a method for using the water-floating microbial pesticide.

18 Claims, 1 Drawing Sheet

WATERBORNE MICROBIAL PESTICIDES

This application is the national phase under 35 U.S.C. §371 of prior PCT International Application No. PCT/JP97/04800 which has an International filing date of Dec. 24, 1997 which designated the United States of America, the entire contents of which are hereby incorporated by reference.

TECHNICAL FIELD OF THE INVENTION

The present invention relates to a water-floating microbial pesticide, a method for producing the microbial pesticide and a method for using the microbial pesticide.

BACKGROUND OF THE INVENTION

For controlling weeds, chemical herbicides have been mainly used. However, serious problems including environmental pollution have been arisen in last several years from the excessive use of chemical pesticides and, therefore, development of weed control agents employing no chemical substances and methods for utilizing such weed control agents have been demanded. In particular, microbial pesticides employing pathogenic microorganisms against weeds have been strongly contemplated. Examples of such microbial pesticides, including some commercially available ones which have been registered, are "DeVine" which is a herbicide against Stranglervine (Asclepiadaceae) developed in the United States, "Collego" which is a herbicide against Northern jointvetch (Leguminosae) developed in the United States and "BioMal" which is a herbicide against Round-leaved mallow (Malvacceae) developed in Canada.

"Collego" is usually sold as a set composed of powder containing spores as the effective ingredient and a solution containing sucrose for suspending the powder therein. These two components must be mixed with each other and diluted with water before use, which requires a great deal of labor. In addition, in such a formulation, raising of powder in the air tends to be caused. "DeVine" is sold in the form of a concentrate solution of the microorganism cells. This herbicide also has a defect in that it can not be stored for a long period of time. [Weed Science 34 (Suppl. 1) (1986):15–16]

In recent years, in the United States and Canada, for the purpose of making the microbial herbicides as mentioned above applicable to plowed fields, improving the adhesion properties of the microbial herbicides to the target weeds and imparting moisture retention on leaves of the weed to make it easy for the microbial herbicides to penetrate in host weeds, studies have been made on using a W/O type surfactant (emulsifier) [Weed Technology 5 (1991) :442–444]. W/O type surfactants have been mainly used in the fields of cosmetics and foods and are generally commercially available. However, such surfactants have been rarely used in pesticides. When a W/O type surfactant is used, the finished pesticide must be applied with a specially designed spreader, which is disadvantageous in practical use. Further, when lecithin derived from. crude plant oil is used as the W/O type surfactant, problems in quality control of a lecithin product would arise owing to lot-to-lot variation in lecithin content, color variation in the crude oil and malodor of the lecithin product. Therefore, such formulation has not been practically used yet.

On the other hand, in recent years in Japan, microbial herbicides employing pathogenic microorganisms against weeds have also been studied. In particular, the development of microbial herbicides against *Echinochloa crus-galli* has been advanced. For example, as such microbial herbicides applicable to paddy fields, those employing as effective ingredient *Cochliobolus lunatus* [Weed Research (1987), 27, 43–47; Japanese Patent Application Laid-open No. 5-284963], *Ustilago trichophora* [WO93/05656], and *Drechslera monoceras* (another name of *Exserohilum monoceras*) [Japanese Patent Application Laid-open Nos. 3-219883, 4-226905, 4-360678, 4-370090, 6-277042, 6-329513, 6-247822, 7-31467, 7-79784 and 8-175917] have been known. It has also been proposed to formulate a herbicide containing a pathogenic microorganism against *Echinochloa crus-galli* alone or in combination with a base component of a conventional chemical herbicide in the similar manner as those for formulating a conventional chemical herbicide [Japanese Patent Application Laid-open Nos. 4-226905 and 4-360678]. However, these formulations have same forms as those of conventional chemical herbicides. For example, a granular formulation tends to settle on paddy sail in water, so that the pathogenic microorganisms contained in the granular formulation have little chance to adhere onto the leave of *Echinochloa crus-galli*, resulting in low herbicidal activity. Wettable powders have also been considered to have problems such as uneven spreadability onto the field, raising of powder in the air which is observed when diluted with water upon use, and the like. Furthermore, such wettable powders have not been used as herbicides for paddy fields because of their inconvenience in treatment and handling. Liquid formulations including floable formulations also have disadvantages such as poor storage properties. Oil formulations have also been developed which are designed to spread the pathogenic microorganisms contained therein over water surface [Japanese Patent Application Laid-open No. 6-179243]. However, such oil formulations have a problem in storage since they should be treated as hazardous materials. Furthermore, in such an oil formulation as disclosed in Japanese Patent Application Laid-open No. 6-179243, the dropwise application to a paddy field would be adversely influenced by wind blowing, and therefore, if it is directly splashed and adhered onto the leaf surface of the cultured rice plants, it would damage the rice plants. For controlling weeds (e.g., *Echinochloa crus-galli*) or insect pests (e.g., water weevil (*Lissorhoptrus orvzophilue*)) in paddy fields, it has been known that it is effective to attack the weeds or the insect pests on the water surface. In view of this knowledge, water-floating chemical pesticides have been developed [Japanese Patent Application Laid-open No. 5-78204], in which glassy mineral and pumice are used as carriers. However, such carrier materials are not useful for formulation of microbial pesticides since they have poor adhesive property with microorganisms.

BRIEF SUMMARY OF THE INVENTION

As described above, the conventional methods for formulating pesticides could not provide water-floating microbial pesticides having easy handling and excellent storage properties. The present invention provides novel water-floating microbial pesticides having easy handling and excellent storage properties.

DETAILED DESCRIPTION OF THE INVENTION

In these situations, for solving problems accompanied with the conventional chemical pesticides applicable to paddy fields including environmental pollution, the present inventors have made extensive and intensive studies on developing microbial pesticides having easy handling properties for application to paddy fields under flooding. As a result, the present inventors have found that a microbial pesticide which spreads over water surface rapidly like oil formulations and floable formulations, floats on water, and exerts herbicidal and insecticidal effects on water surface can be produced by coating a microorganism with oil containing a W/O type (water-in-oil type) surfactant and further coating the oil-coated microorganism with powder having a low bulk specific gravity in a form of powder or granule. This finding leads the completion of the present invention.

Accordingly, the present invention relates to a water-floating microbial pesticide comprising a microorganism, a W/O type surfactant, oil, and powder having a low bulk specific gravity, a method for producing the microbial pesticide and, a method for using the microbial pesticide.

Unlike conventional granular pesticides, the microbial pesticide of the present invention does not sediment in water and can float on water for a long period of time, and therefore can effectively act on weeds such as *Echinochloa crus-galli* and insect pests such as water weevil (*Lissorhoptrus orvzophilue*). Furthermore, unlike conventional floable pesticides and oil-type pesticides, the microbial pesticide of the present invention has no problem in storage and handling. Still further, since the microbial pesticide of the present invention employs a microorganism as an effective ingredient, it has extremely low influence on environment.

The present invention will be described more specifically below.

(1) Preparation of Microbial Pesticide of the Invention

The microbial pesticide of the present invention can be prepared by suspending a microorganism in water, adding oil containing a W/O type surfactant to the resultant suspension and mixing with each other, and further adding powder with a small specific gravity to the mixture.

The microorganism used in the microbial pesticide of the present invention may be any one as long as it acts as an effective ingredient of the microbial pesticide. Such microorganisms include those having a herbicidal activity, those having an insecticidal activity and those having an antimicrobial activity. Specific examples of the microorganism having a herbicidal activity include fungi belonging to the genera Acremonium, Alternaria, Bipolaris, Cephalosporium, Cercospora, Cochlioborus, Colletotrichum, Curvularia, Drechslera, Epiccocosorus, Exserohirum, Fusarium, Nimbya, Phytophthora, Puccinia, Sclerotinia and Ustiiago. Among them, especially preferred are *Exserohilum monoceras* B026, *Exserohilum monoceras* B232, *Exserohilum monoceras* B263, *Exserohilum monoceras* B267 and *Exserohilum monoceras* B276, all of which were deposited on Mar. 5, 1993 with the National Institute of Bioscience and Human-Technology, Agency of Industrial Science and Technology (1-3, Higashi 1-chome, Tsukuba-shi, Ibaraki-ken, Japan) under the Accession Nos. FERM BP-4215, FERM BP-4217, FERM BP-4218, FERM BP-4219 and FERM BP-4220, respectively; *Exserohilum monoceras* JTB-012, *Exserohilum monoceras* JTB-013, *Exserohilum monoceras* JTB-799, *Exserohilum monoceras* JTB-803 and *Exserohilum monoceras* JTB-808, all of which were deposited on Oct. 27, 1995 with the National Institute of Bioscience and Human-Technology, Agency of Industrial Science and Technology (1-3, Higashi 1-chome, Tsukuba-shi, Ibaraki-ken, Japan) under the Accession Nos. FERM BP-5271, FERM BP-5272, FERM BP-5273, FERM BP-5274 and FERM BP-5275, respectively; Curvularia sp. B-261, Curvularia sp. B-236, Curvularia sp. B-245, all of which were deposited on March 4, 1992 with the National Institute of Bioscience and Human-Technology, Agency of Industrial Science and Technology (1-3, Higashi 1-chome, Tsukuba-shi, Ibaraki-ken, Japan) under the Accession Nos. FERM BP-4249, FERM BP-4248 and FERM BP-4247, respectively; *Nimbya scirpicola* K-004 of which was deposited on Jun. 2, 1990 with the National Institute of Bioscience and Human-Technology, Agency of Industrial Science and Technology (1-3, Higashi 1-chome, Tsukuba-shi, Ibaraki-ken, Japan) under the Accession No. FERM BP-4448 and *Epiccocosorus nematosporus* K-035 of which was deposited on Nov. 25, 1993 with the National Institute of Bioscience and Human-Technology, Agency of Industrial Science and Technology (1-3, Higashi 1-chome, Tsukuba-shi, Ibaraki-ken, Japan) under the Accession No. FERM BP-4477. These microorganisms have conidia having hydrophobic surface. Therefore, the use of their conidia in a dried form has a disadvantage they are easily raised in the air. The process of the present invention can improve such disadvantage and enables to treat such dried conidia easily and safety. These microorganisms are preferably used in a form of asexual spore such as conidium, but may also be used in a form of sexual spore or mycelium. In the present invention, the amount of the microorganism used is not particularly limited as long as it is effective for providing satisfactory pesticidal properties to the final pesticide and may vary depending on the species of the microorganism employed. For example, when conidium of *Exserohilum monoceras* is used, the final content of conidia in the formulation of microbial pesticide is preferably $1 \times 10^3$ to $1 \times 10^9$ conidia/g, more preferably $1 \times 10^5$ to $1 \times 10^8$ conidia/g; whereas when conidium of Curvularia sp. is used, the final content of conidia in the formulation of microbial pesticide is preferably $1 \times 10^5$ to $1 \times 10^{12}$ conidia/g, more preferably $1 \times 10^7$ to $1 \times 10^1$ conidia/g. The spores of the microorganism used in the microbial pesticide of the invention can be prepared by any conventional method. For example, conidium of a microorganism belonging to the genus Exserohilum can be readily prepared by inoculating the microorganism cells onto oatmeal sucrose agar medium, a V8 juice agar medium, etc. and then culturing the medium at 25° C. for 20 days.

In the present invention, the microorganism may be coated with the oil directly. However, it is preferred to mix the microorganism with a mineral carrier prior to coating the microorganism with the oil. The mineral carrier used is not particularly limited, but is preferably a porous type one such as diatomaceous earth, zeolite and white carbon. The coating of the microorganism with a mineral carrier enables to supply air and moisture necessary for growth of the microorganism through the mineral carrier and consequently improve the durability of the microorganism in the final pesticide. In the present invention, it is more preferred to incorporate a binder to the mixture of the microorganism and the mineral oil to improve the adhesion property of the mineral carrier to the microorganism. Examples of such binder include soluble starch, gum arabic, xanthan gum, carrageenin gum, lignin sulfonate, hydroxyethyl cellulose (HEC) and carboxymethyl cellulose (CMC).

Examples of the oil used in the present invention include but not limited to plant oils such as soy bean oil, rapeseed oil, caster oil, cotton seed oil, rice bran oil, palm oil, olive oil, safflower oil and jojoba oil; mineral oils such as spindle oil, heavy white oil, light white oil, mineral spirit, mineral turpentine, naphtene oil, paraffin oil and machine oil for microbial pesticides; silicone oil and other silicon-containing oil; and the like. The amount of the oil used is not particularly limited. However, it is preferable to use the oil in the final microbial pesticide in an amount of 10 to 70%, preferably 10 to 50% based on the weight of the final microbial pesticide.

In the present invention, the oil is admixed with a W/O type surfactant prior to mixing with the microorganism. The surfactant used is not particularly limited as long as it has a low HLB (hydrophile-lypophile balance) value. However, it is preferred to use a surfactant having an HLB value within the range of 3 to 7. Preferably used as such surfactant is a nonionic surfactant such as polyglyceryl stearate type, polyglyceryl oleate type, monoglycerol ester type, sorbitane stearate type, sorbitane oleate type, sorbitane ester type, nonylphenol type and glycerol fatty acid ester type ones. Specific examples of such surfactant include: as polyglyceryl stearate type, "Hostacerin WOL" [polyglyceryl-2-sesquisisostearate] (Hoechst); as polyglyceryl oleate, "Hostacerin DGO" [polyglyceryl-2-sesquiisooleate] (Hoechst); as monoglycerol ester type, "Kadenax GS-90" (Lion Corporation); as sorbitan stearate type, "Leodol SP-S10" [sorbitan monostearate] (Kao Corporation), "Leodol AS-10" [sorbitan monostearate] (Kao Corporation), "Emasol S-10" [sorbitan monostearate] (Kao Corpoation) and "Emasol S-20" [sorbitan distearate] (Kao Corporation); as sortitan oleate type, "Leodol SP-010" [sorbitan monooleate] (Kao Corporation), "Leodol AO-10" [sorbitan monooleate] (Kao Corporation), "Emasol O-10" [sorbitan monooleate] (Kao Corporation) and "Emasol O-15R" [sorbitan sesquioleate] (Kao Corporation); as sorbitan ester type, "Kadenax SO-80" (Lion Corporation) and "Kadenax SO-80C" (Lion Corporation); as nonyl phenol type, "Liponox NC-10" (Lion Corporation), "Liponox NC-20" (Lion Corporation); and glycerol fatty acid esters.

The amount of the surfactant used is not particularly limited. However, it is preferred for the surfactant to be used in an amount of 0.1 to 10%, preferably 1 to 5% based on the weight of the final microbial pesticide.

In addition, a viscosity modifier may be added to the mixture of the oil and the W/O type surfactant to control the viscosity of the oil. Examples of such viscosity modifier include lanolin, vaseline, beeswax and glycerol. The amount of the viscosity modifier used is also not particularly limited. However, it is preferred for the viscosity modifier to be used in an amount of 0 to 60%, preferably 5 to 20% based on the weight of the finished microbial pesticide.

In the microbial pesticide of the present invention, a phthalic acid-based compound such as diisononyl phthalate (DINP), diisodecyl phthalate (DIDP) and dioctyl phthalate (DOP) may be added to improve the developing property over water surface of the final microbial pesticide. The amount of such compound used is not particularly limited. However, it is preferred for the compound to be used in an amount of 0 to 20%, preferably 5 to 15% based on the weight of the final microbial pesticide.

In the present invention, an emulsion stabilizer such as an aluminum or magnesium salt of stearic acid or glycerol tristearate may also be used in the microbial pesticide to stabilize the W/O emulsion of the oil. The amount of such emulsion stabilizer used is not particularly limited. However, it is preferred for the emulsion stabilizer to be used in an amount of 0 to 5%, preferably 0 to 2% based on the weight of the final microbial pesticide.

Besides the above-mentioned components, the microbial pesticide of the present invention may contain other additives as required. Examples of such additives include nitrogen sources (e.g., nitrates, ammonia, amino acids, etc.) and carbon sources effective for growth of the microorganism; substances capable of accelerating the germination of spores of the microorganism (e.g., carboxymethyl cellulose sodium salt, sodium naphthalene sulfonate-formalin condensate, polyethylene glycol, etc.); humectants (e.g., polysaccharides such as hyaluronic acid, collagen, amino acids, proteins, glycerol, oils and fats, etc.); and the like.

As the powder having a low bulk specific gravity used in the present invention, any one may be employed as long as it has a specific gravity of not more than 1. However, preferably used as such powder are white carbons (e.g., "Carplex 67" and "Carplex 80", products by Shionogi & Co., Ltd.; "Hisil 233", a product by Sanyo Trading Co., Ltd.; etc.) and active carbon. The amount of the powder used is not particularly limited. However, it is preferred for the powder to be used in an mount of 10 to 80%, preferably 30 to 60% based on the amount of the final microbial pesticide.

The above-mentioned components are mixed, dried and then ground to thereby obtain the microbial pesticide of the present invention in a powdery or granular form.

The process for producing the microbial pesticide of the present invention will be illustrated below with reference to FIG. 1.

Figures 1, 1A:
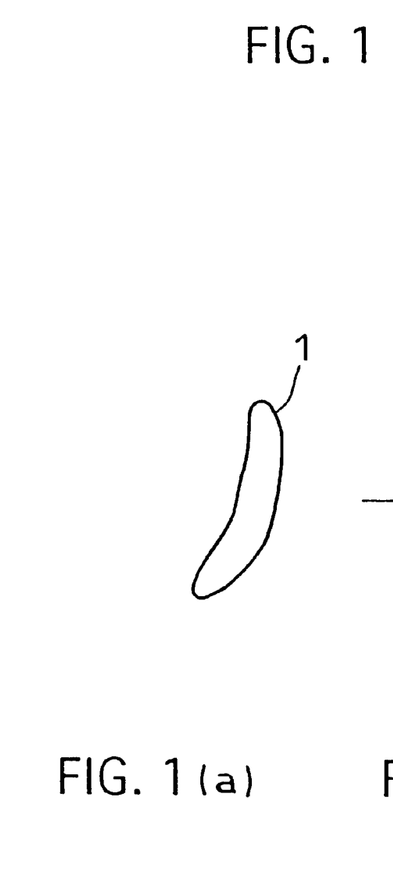
FIG. 1 is a schematic diagram of the process for producing the microbial pesticides of the invention.
Figure 1B:
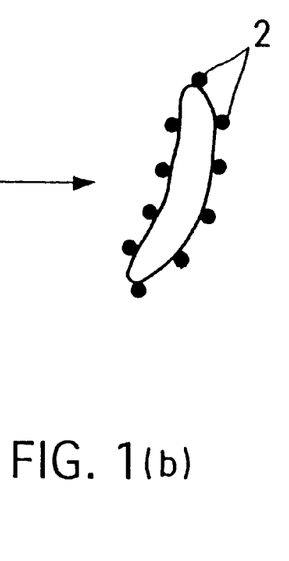
Figure 1C:
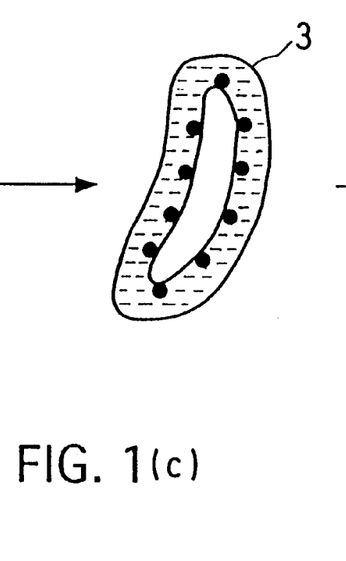
Figure 1D:
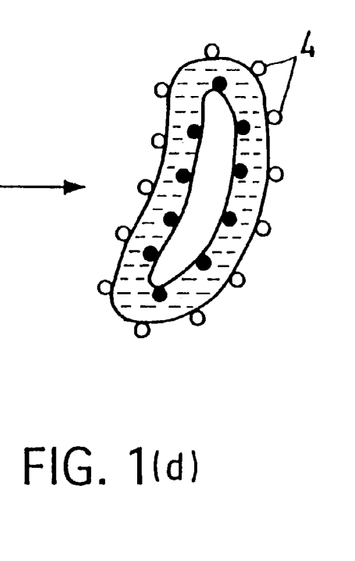

Spore 1 of a microorganism used generally has a bulk specific gravity of 1 or higher and does not float in water by itself (FIG. 1a). To a suspension of spore 1 are added a binder (e.g., carboxymethyl cellulose) and a mineral carrier (e.g., diatomaceous earth), whereby particles 2 of the mineral carrier allow to adhere to the periphery of spore 1 (FIG. 1b). Subsequently, an oil (specific gravity: about 0.7) containing a W/O type surfactant is added to the suspension of spore 1 and mixed with each other to form oil layer 3 surrounding spore 1 (FIG. 1c). To the resultant is added powder having a low bulk specific gravity such as white carbon (specific gravity: about 0.25) and mixed, whereby particles 4 of the powder allow to adhere to the outer periphery of oil layer 3 (FIG. 1d). In this manner, an microbial pesticide comprising spores of a microorganism capable of floating in water can be prepared.

(2) Method For Using of the Microbial Pesticide of the Invention

The microbial pesticide of the present invention can be used as a herbicide against weeds in a paddy field, particularly against *Echinochloa crus-galli*. Besides as herbicide, the above-mentioned formulation can also be used as an insecticide, a disease control agent for plants or the like depending on the nature and the properties of the microorganism employed.

When the microbial pesticide of the invention is used as a herbicide, the microbial pesticide may be applied to weeds in any growth stage. However, because of the floating property on water of the microbial pesticide, it is especially effective to apply the microbial pesticide to weeds in early growth stage under conditions where their plant bodies are submarged in a paddy field. For example, for controlling *Echinochloa crus-galli* in a paddy field which is flooded to 3–10 cm in water depth, it is effective to apply the microbial pesticide to the weed in 2-leaf stage or earlier. The microbial pesticide of the present invention containing any of the above-mentioned microorganisms has no influence on the growth of a rice plant which is a useful crop in a paddy field.

When the microbial pesticide of the invention is used for controlling weeds in a paddy field, the microbial pesticide may be applied in any manner as long as the weeds are effectively controlled. However, it is preferably for the microbial pesticide to be applied to a paddy filed under flooding. In this case, the season for application of the microbial pesticide to a paddy field is not particularly limited. However, since the microbial pesticide of the invention is particularly effective against seedlings in submarged, it is preferably for the microbial pesticide to be applied to a paddy field after paddling, preferably soon after transplanting of rice seedlings.

On the other hand, when the microbial pesticide of the invention is used for controlling weeds in a field, its dosage may vary depending on the species of the microorganisms employed. For example, when *Exserohilum monoceras* is employed, it is preferred for the microbial pesticide to be applied to a plowed field in a dose amount of $1\times10^6$ to $1\times10^5$ conidia/10-are, preferably $1\times10^7$ to $1\times10^{12}$ conidia/10-are in terms of the population of conidia of the microorganism; whereas when Culvularia sp. is employed, it is preferred to be applied to a field in a dose amount of $1\times10^7$ to $1\times10^6$ conidia/10-are, preferably $1\times10^8$ to $1\times10^3$ conidia/10-are in terms of the population of conidia of the microorganism.

EXAMPLES

Formulation Example 1: (Fine Granular Formulation)

To a mixture of diatomaceous earth (Oplite P-1200, a product by Hokushu Keisoudo; 5 g) and carboxymethyl cellulose (Celogen 7A, a product by Dai-ichi Kogyo Seiyaku Co., Ltd.; 0.1 g) was added a suspension of conidia of *Exserohilum monoceras* JTB-808 ($10^9$ conidia) in 40 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (40 g) was blended with the above-prepared conidium suspension and further blended with white carbon (Carplex 80, a product by Shionogi & Co., Ltd.; 48 g). The resultant mixture was dried in air, and the dried mass was ground to obtain fine granules having a particle size distribution of 105–300 µm.

Formulation Example 2: (Fine Granular Formulation)

To a mixture of diatomaceous earth (Oplite P-1200, a product by Hokushu Keisoudo; 5 g) and carboxymethyl cellulose (Celogen 7A, a product by Dai-ichi Kogyo Seiyaku Co., Ltd.; 0.1 g) was added a suspension of conidia of *Exserohilum monoceras* JTB-808 ($10^9$ conidium) in 40 mL of water and mixed with each other. Hostaserin WOL (a product by Hoechst; 10.0%), castor oil (a product by-Wako Pure Chemical Industries, Ltd.; 62.9%), lanolin (a product by Wako Pure Chemical Industries, Ltd.; 12.7%), paraffin wax (a product by Wako Pure Chemical Industries, Ltd.; 6.4%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (40 g) was blended with the above-prepared conidium suspension and further blended with white carbon (Carplex 80, a product by Shionogi & Co., Ltd.; 48 g). The resultant mixture was dried in air, and the dried mass was ground to obtain fine granules having a particle size distribution of 105–300 µm.

Formulation Example 3: (Fine Granular Formulation)

To a mixture of diatomaceous earth (Oplite P-1200, a product by Hokushu Keisoudo; 5 g) and carboxymethyl cellulose (Celogen 7A, a product by Dai-ichi Kogyo Seiyaku Co., Ltd.; 0.1 g) was added a suspension of conidia of *Exserohilum monoceras* JTB-808 ($10^9$ conidia) in 40 mL of water and mixed with each other. Hostaserin WOL (a product by Hoechst; 9.7%), jojoba oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (40 g) was blended with the above-prepared conidium suspension and further blended with white carbon (Carplex 80, a product by Shionogi & Co., Ltd.; 48 g). The resultant mixture was dried in air, and the dried mass was ground to obtain fine granules having a particle size distribution of 105–300 µm.

Formulation Example 4: (Fine Granular Formulation)

To a mixture of diatomaceous earth (Oplite P-1200, a product by Hokushu Keisoudo; 5 g) and carboxymethyl cellulose (Celogen 7A, a product by Dai-ichi Kogyo Seiyaku Co., Ltd.; 0.1 g) was added a suspension of conidia of *Exserohilum monoceras* JTB-808 ($10^9$ conidia) in 40 mL of water and mixed with each other. Liponox NC-10 (a product by Lion corporation; 10%), castor oil (a product by Wako Pure Chemical Industries, Ltd.; 65%), lanolin (a product by Wako Pure Chemical Industries, Ltd.; 15%), paraffin wax (a product by Wako Pure Chemical Industries, Ltd.; 8%), aluminum stearate (a product by Wako Pure Chemical Industries, Ltd.; 0.7%) and magnesium stearate (a product by Wako Pure Chemical Industries, Ltd.; 1.3%) were mixed at 80° C. to obtain a homogeneous oil mixture. After cooling to room temperature, this oil mixture (40 g) was blended with the above-prepared conidium suspension and further blended with white carbon (Carplex 80, a product by Shionogi & Co., Ltd.; 48 g). The resultant mixture was dried in air, and the dried mass was ground to obtain fine granules having a particle size distribution of 105–300 µm.

Formulation Example 5: (Fine Granular Formulation)

To a mixture of diatomaceous earth (Oplite P-1200, a product by Hokushu Keisoudo; 5 g) and carboxymethyl cellulose (Serogen 7A, a product by Dai-ichi Kogyo Seiyaku Co., Ltd.; 0.1 g) was added a suspension of conidia of *Exserohilum monoceras* JTB-808 ($10^9$ conidia) in 40 mL of water and mixed with each other. Kadenax GS9 (a product by Lion corporation; 10%), castor oil (a product by Wako Pure Chemical Industries, Ltd.; 65%), lanolin (a product by Wako Pure Chemical Industries, Ltd.; 1%), paraffin wax (a product by Wako Pure Chemical Industries, Ltd.; 8%), aluminum stearate (a product by Wako Pure Chemical Industries, Ltd.; 0.7%) and magnesium stearate (a product by Wako Pure Chemical Industries, Ltd.; 1.3%) were mixed at 80° C. to obtain a homogeneous oil mixture. After cooling to room temperature, this oil mixture (40 g) was blended with the above-prepared conidium suspension and further blended with white carbon (Carplex 80, a product by Shionogi & Co., Ltd.; 48 g). The resultant mixture was dried in air, and the dried mass was ground to obtain fine granules having a particle size distribution of 105–300 µm.

Formulation Example 6: (Fine Granular Formulation)

To a mixture of diatomaceous earth (Oplite P-1200, a product by Hokushu Keisoudo; 5 g) and carboxymethyl cellulose (Serogen 7A, a product by Dai-ichi Kogyo Seiyaku Co., Ltd.; 0.1 g) was added a suspension of conidia of *Exserohilum monoceras* JTB-808 ($10^9$ conidia) in 40 mL of water and mixed with each other. Castor oil (a product by Wako Pure Chemical Industries, Ltd.; 75%), lanolin (a product by Wako Pure Chemical Industries, Ltd.; 9.3%), paraffin wax (a product by Wako Pure Chemical Industries, Ltd.; 4.3%), a glycerol fatty acid ester (a product by Wako Pure Chemical Industries, Ltd.; 9.3%), aluminum stearate (a product by Wako Pure Chemical Industries, Ltd.; 0.7%) and magnesium stearate (a product by Wako Pure Chemical Industries, Ltd.; 1.4%) were mixed at 80° C. to obtain a homogeneous oil mixture. After cooling to room temperature, this oil mixture (40 g) was blended with the above-prepared conidium suspension and further blended with white carbon (Carplex 80, a product by Shionogi & Co., Ltd.; 48 g). The resultant mixture was dried in air, and the dried mass was ground to obtain fine granules having a particle size distribution of 105–300 μm.

Formulation Example 7: (Fine Granular Formulation)

To a mixture of diatomaceous earth (Oplite P-1200, a product by Hokushu Keisoudo; 5 g) and carboxymethyl cellulose (Serogen 7A, a product by Dai-ichi Kogyo Seiyaku Co., Ltd.; 0.1 g) was added a suspension of conidia of *Exserohilum monoceras* JTB-808 ($10^9$ conidia) in 40 mL of water and mixed with each other. Castor oil (a product by Wako Pure Chemical Industries, Ltd.; 71%), lanolin (a product by Wako Pure Chemical Industries, Ltd.; 14.3%), paraffin wax (a product by Wako Pure Chemical Industries, Ltd.; 7.7%), glycerol tristearate (a product by Wako Pure Chemical Industries, Ltd.; 1.4%), sorbitan monostearate (a product by Wako Pure Chemical Industries, Ltd.; 2.8%) and POE (20) sorbitan monostearate (a product by Wako Pure Chemical Industries, Ltd.; 2.8%) were mixed at 80° C. to obtain a homogeneous oil mixture. After cooling to room temperature, this oil mixture (40 g) was blended with the above-prepared conidium suspension and further blended with white carbon (Carplex 80, a product by Shionogi &, Co., Ltd.; 48 g). The resultant mixture was dried in air, and the dried mass was ground to obtain fine granules having a particle size distribution of 105–300 μm.

Formulation Example 8: (Fine Granular Formulation)

To a mixture of diatomaceous earth (Oplite P-1200, a product by Hokushu Keisoudo; 5 g) and carboxymethyl cellulose (Serogen 7A, a product by Dai-ichi Kogyo Seiyaku Co., Ltd.; 0.1 g) was added a suspension of conidia of *Exserohilum monoceras* JTB-808 ($10^9$ conidia) in 40 mL of water and mixed with each other. Kadenax SO-80 (a product by Lion Corporation; 10.3%), rapeseed oil (51.5%), lanolin (a product by Wako Pure Chemical Industries, Ltd.; 19.3%), paraffin wax (a product by Wako Pure Chemical Industries, Ltd.; 10.3%), a glycerol fatty acid ester (a product by Wako Pure Chemical Industries, Ltd.; 4.3%) and glycerol (a product by Wako Pure Chemical Industries, Ltd.; 4.3%) were mixed at 80° C. to obtain a homogeneous oil mixture. After cooling to room temperature, this oil mixture (40 g) was blended with the above-prepared conidium suspension and further blended with white carbon (Carplex 80, a product by Shionogi & Co., Ltd.; 48 g). The resultant mixture was dried in air, and the dried mass was ground to obtain fine granules having a particle size distribution of 105–300 μm.

Formulation Example 9: (Fine Granular Formulation)

To a mixture of diatomaceous earth (Oplite P-1200, a product by Hokushu Keisoudo; 5 g) and carboxymethyl cellulose (Serogen 7A, a product by Dai-ichi Kogyo Seiyaku Co., Ltd.; 0.1 g) was added a suspension of conidia of *Exserohilum monoceras* JTB-808 ($10^9$ conidia) in 40 mL of water and mixed with each other. Hostaserin DGO (a product by Hoechst; 10%), castor oil (a product by Wako Pure Chemical Industries, Ltd.; 50%), DIDP (12.6%), lanolin (a product by Wako Pure Chemical Industries, Ltd.; 12.6%), paraffin wax (a product by Wako Pure Chemical Industries, Ltd.; 6.4%), a glycerol fatty acid ester (a product by Wako Pure Chemical Industries, Ltd.; 4.2%) and glycerol (a product by Wako Pure Chemical Industries, Ltd.; 4.2%) were mixed at 80° C. to obtain a homogeneous oil mixture. After cooling to room temperature, this oil mixture (40 g) was blended with the above-prepared conidium suspension and further blended with white carbon (Carplex 80, a product by Shionogi & Co., Ltd.; 48 g). The resultant mixture was dried in air, and the dried mass was ground to obtain fine granules having a particle size distribution of 105–300 μm.

Formulation Example 10: (Fine Granular Formulation)

A suspension of conidia of *Exserohilum monoceras* JTB-808 ($10^8$ conidia) in 40 mL of water was prepared. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (0.75 g) was blended with the above-prepared conidium suspension and further blended with white carbon (Carplex 80, a product by Shionogi & Co., Ltd.; 1.5 g). The resultant mixture was dried in air, and the dried mass was ground to obtain fine granules having a particle size distribution of 105–300 μm.

Formulation Example 11: (Fine Granular Formulation)

To a mixture of diatomaceous earth (Oplite P-1200, a product by Hokushu Keisoudo; 0.5 g) and carboxymethyl cellulose (Serogen 7A, a product by Dai-ichi Kogyo Seiyaku Co., Ltd.; O.Olg) was added a suspension of conidia of *Exserohilum monoceras* JTB-808 ($10^8$ conidia) in 40 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (0.75 g) was blended with the above-prepared conidium suspension and further blended with white carbon (Carplex 80, a product by Shionogi & Co., Ltd.; 1.5 g). The resultant mixture was dried in air, and the dried mass was ground to obtain fine granules having a particle size distribution of 105–300 μm.

Formulation Example 12: (Fine Granular Formulation)

To a mixture of diatomaceous earth (Oplite P-1200, a product by Hokushu Keisoudo; 0.5 g) and carboxymethyl cellulose (Serogen 7A, a product by Dai-ichi Kogyo Seiyaku Co., Ltd.; 0.Olg) was added a suspension of conidia of *Exserohilum monoceras* JTB-808 ($10^8$ conidia) in 40 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (1.0 g) was blended with the above-prepared conidium suspension and further blended with white carbon (Carplex 80, a product by Shionogi & Co., Ltd.; 1.5 g). The resultant mixture was dried in air, and the dried mass was ground to obtain fine granules having a particle size distribution of 105–300 µm.

Formulation Example 13: (Fine Granular Formulation)

To a mixture of diatomaceous earth (Oplite P-1200, a product by Hokushu Keisoudo; 0.5 g) and carboxymethyl cellulose (Serogen 7A, a product by Dai-ichi Kogyo Seiyaku Co., Ltd.; 0.1 g) was added a suspension of conidia of *Exserohilum monoceras* JTB-808 ($10^8$ conidia) in 40 mL of water and mixed with each other. Hostaserin WOL (a product by Hoechst; 9.7%), light white oil (a product by Sigma; 48.4%), lanolin (Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (1.25 g) was blended with the above-prepared conidium suspension and further blended with white carbon (Carplex 80, a product by Shionogi & Co., Ltd.; 1.5 g). The resultant mixture was dried in air, and the dried mass was ground to obtain fine granules having a particle size distribution of 105–300 μm.

Formulation Example 14: (Fine Granular Formulation)

To a mixture of diatomaceous earth (Oplite P-1200, a product by Hokushu Keisoudo; 1.0 g) and carboxymethyl cellulose (Serogen 7A, a product by Dai-ichi Kogyo Seiyaku Co., Ltd.; 0.1 g) was added a suspension of conidia of *Exserohilum monoceras* JTB-808 ($10^8$ conidia) in 40 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (1.5 g) was blended with the above-prepared conidium suspension and further blended with white carbon (Carplex 80, a product by Shionogi & Co., Ltd.; 3.0 g). The resultant mixture was dried in air, and the dried mass was ground to obtain fine granules having a particle size distribution of 105–300 μm.

Formulation Example 15: (Fine Granular Formulation)

To a mixture of diatomaceous earth (Oplite P-1200, a product by Hokushu Keisoudo; 1.0 g) and carboxymethyl cellulose (Serogen 7A, a product by Dai-ichi Kogyo Seiyaku Co., Ltd.; 0.01 g) was added a suspension of conidia of *Exserohilum monoceras* JTB-808 ($10^8$ conidia) in 40 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (2.0 g) was blended with the above-prepared conidium suspension and further blended with white carbon (Carplex 80, a product by Shionogi & Co., Ltd.; 3.0 g). The resultant mixture was dried in air, and the dried mass was ground to obtain fine granules having a particle size distribution of 105–300 μm.

Formulation Example 16: (Fine Granular Formulation)

To a mixture of diatomaceous earth (Oplite P-1200, a product by Hokushu Keisoudo; 1.0 g) and carboxymethyl cellulose (Serogen 7A, Dai-ichi Kogyo Seiyaku Co., Ltd.; 0.1 g) was added a suspension of conidia of *Exserohilum monoceras* JTB-808 ($10^8$ conidia) in 40 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd. ; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (2.5 g) was blended with the above-prepared conidium suspension and further blended with white carbon (Carplex 80, a product by Shionogi & Co., Ltd.; 3.0 g). The resultant mixture was dried in air, and the dried mass was ground to obtain fine granules having a particle size distribution of 105–300 μm.

Formulation Example 17: (Fine Granular Formulation)

To a mixture of diatomaceous earth (Oplite P-1200, a product by Hokushu Keisoudo; 2.0 g) and carboxymethyl cellulose (Serogen 7A, a product by Dai-ichi Kogyo Seiyaku Co., Ltd.; 0.02 g) was added a suspension of conidia of *Exserohilum monoceras* JTB-808 ($10^9$ conidia) in 40 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (4.0 g) was blended with the above-prepared conidium suspension and further blended with white carbon (Carplex 80, a product by Shionogi & Co., Ltd.; 4.4 g). The resultant mixture was dried in air, and the dried mass was ground to obtain fine granules having a particle size distribution of 105–300 μm.

Formulation Example 18: (Fine Granular Formulations)

To a mixture of diatomaceous earth (Oplite P-1200, a product by Hokushu Keisoudo; 15.68 g) and carboxymethyl cellulose (Serogen 7A, a product by Dai-ichi Kogyo Seiyaku Co., Ltd.; 0.32 g) was added a suspension of conidia of *Exserohilum monoceras* JTB-808 ($10^9$ conidia) in 50 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (40 g) was blended with the above-prepared conidium suspension and further blended with white carbon (Carplex 80, a product by Shionogi & Co., Ltd.; 48 g). The resultant mixture was dried in air, and the dried mass was ground to obtain seven kinds of fine granules each having a particle size distribution of >1700, 1700-710, 710-300, 300-212, 212-106, 106-63 and 63>μm, respectively.

Formulation Example 19: (Fine Granular Formulation)

To a mixture of diatomaceous earth (Oplite P-1200, a product by Hokushu Keisoudo; 3.36 g) and carboxymethyl cellulose (Serogen 7A, a product by Dai-ichi Kogyo Seiyaku Co., Ltd.; 0.06 g) was added a suspension of conidia of *Exserohilum monoceras* JTB-808 ($10^9$ conidia) in 40 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (8 g) was blended with the above-prepared conidium suspension and further blended with white carbon (Carplex 80, a product by Shionogi & Co., Ltd.; 9.6 g). The resultant mixture was dried in air, and the dried mass was ground to obtain fine granules having a particle size distribution of 105–300 μm.

Formulation Example 20: (Fine Granular Formulation)

To a mixture of diatomaceous earth (Oplite P-1200, a product by Hokushu Keisoudo; 3.36 g) and carboxymethyl cellulose (Serogen 7A, a product by Dai-ichi Kogyo Seiyaku Co., Ltd.; 0.06 g) was added a suspension of conidia of *Exserohilum monoceras* JTB-808 ($2\times10^8$ conidia) in 40 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (8 g) was blended with the above-prepared conidium suspension and further blended with white carbon (Carplex 80, a product by Shionogi & Co., Ltd.; 9.6 g). The resultant mixture was dried in air, and the dried mass was ground to obtain fine granules having a particle size distribution of 105–300 μm.

Formulation Example 21: (Fine Granular Formulation)

To a mixture of diatomaceous earth (Oplite P-1200, a product by Hokushu Keisoudo; 3.36 g) and carboxymethyl cellulose (Serogen 7A, a product by Dai-ichi Kogyo Seiyaku Co., Ltd.; 0.06 g) was added a suspension of conidia of *Exserohilum monoceras* JTB-808 ($0.4\times10^8$ conidia) in 40 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (8 g) was blended with the above-prepared conidium suspension and further blended with white carbon (Carplex 80, a product by Shionogi & Co., Ltd.; 9.6 g). The resultant mixture was dried in air, and the dried mass was ground to obtain fine granules having a particle size distribution of 105–300 μm.

Formulation Example 22: (Fine Granular Formulation)

To a mixture of diatomaceous earth (Oplite P-1200, a product by Hokushu Keisoudo; 55 g) and carboxymethyl cellulose (Serogen 7A, a product by Dai-ichi Kogyo Seiyaku Co., Ltd.; 1.1 g) was added a suspension of conidia of *Exserohilum monoceras* JTB-808 ($10^{10}$ conidia) in 400 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (74.4 g) was blended with the above-prepared conidium suspension and further blended with white carbon (a product by Carplex 80, Shionogi & Co., Ltd.; 154 g). The resultant mixture was dried in air, and the dried mass was ground to obtain fine granules (470 g) having a particle size distribution of 105–300 μm.

Formulation Example 23: (Fine Granular Formulation)

A suspension of conidia of *Exserohilum monoceras* JTB-808 ($10^8$ conidia) in 40 mL of water was prepared. Emasol O-15R (a product by Kao Corporation; 9.7%), light white oil (Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (0.75 g) was blended with the above-prepared conidium suspension and further blended with white carbon (Carplex 80, a product by Shionogi & Co., Ltd.; 1.5 g). The resultant mixture was dried in air, and the dried mass was ground to obtain fine granules having a particle size distribution of 105–300 μm.

Formulation Example 24: (Fine Granular Formulation)

To a mixture of zeolite (synthetic zeolite powder, a product by Wako Pure Chemical Industries, Ltd.; 55 g) and carboxymethyl cellulose (Serogen 7A, a product by Dai-ichi Kogyo Seiyaku Co., Ltd.; 1.1 g) was added a suspension of conidia of *Exserohilum monoceras* JTB-799 ($10^{10}$ conidia) in 400 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (74.4 g) was blended with the above-prepared conidium suspension and further blended with white carbon (Carplex 80, a product by Shionogi & Co., Ltd.; 154 g). The resultant mixture was dried in air, and the dried mass was ground to obtain fine granules having a particle size distribution of 105–300 μm.

Formulation Example 25: (Fine Granular Formulation)

To a mixture of zeolite (Zeolite 150G, a product by Kunimine Kogyo Kabushiki-gaisha; 55 g) and carboxymethyl cellulose (Serogen 7A, a product by Dai-ichi Kogyo Seiyaku Co., Ltd.; 1.1 g) was added a suspension of conidia of *Exserohilum monoceras* JTB-012 ($10^{10}$ conidia) in 400 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (74.4 g) was blended with the above-prepared conidium suspension and further blended with white carbon (Carplex 80, a product by Shionogi & Co., Ltd.; 154 g). The resultant mixture was dried in air, and the dried mass was ground to obtain fine granules having a particle size distribution of 105–300 μm.

Formulation Example 26: (Fine Granular Formulation)

To a mixture of diatomaceous earth (Radiorite 700, a product by Showa chemical Industry Co., Ltd.; 55 g) and carboxymethyl cellulose (Serogen 7A, a product by Dai-ichi Kogyo Seiyaku Co., Ltd.; 1.1 g) was added a suspension of conidia of *Exserohilum monoceras* JTB-013 ($10^{10}$ conidia) in 400 mL of water and mixed with each other. Liponox NC-10 (a product by Lion Corporation; 10%), castor oil (a product by Wako Pure Chemical Industries, Ltd.; 65%), lanolin (a product by Wako Pure Chemical Industries, Ltd.; 15%), paraffin wax (a product by Wako Pure Chemical Industries, Ltd.;8%), aluminum stearate (a product by Wako Pure Chemical Industries, Ltd.; 0.7%) and magnesium stearate (a product by Wako Pure Chemical Industries, Ltd.; 1.3%) were mixed at 80° C. to obtain a homogeneous oil mixture. After cooling to room temperature, this oil mixture (74.4 g) was blended with the above-prepared conidium suspension and further blended with white carbon (Carplex 80, a product by Shionogi & Co., Ltd.; 154 g). The resultant mixture was dried in air, and the dried mass was ground to obtain fine granules having a particle size distribution of 105–300 μm.

Formulation Example 27: (Fine Granular Formulation)

To a mixture of white carbon (Carplex 67, a product by Shionogi & Co., Ltd.; 55 g) and carboxymethyl cellulose (Serogen 7A, a product by Dai-ichi Kogyo Seiyaku Co., Ltd.; 1.1 g) was added a suspension of conidia of *Exserohilum monoceras* B026 ($10^{10}$ conidia) in 400 mL of water and mixed with each other. Emasol O-15R (a product by Kao Corporation; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (74.4 g) was blended with the above-prepared conidium suspension and further blended with white carbon (Carplex 80, a product by Shionogi & Co., Ltd.; 154 g). The resultant mixture was dried in air, and the dried mass was ground to obtain fine granules having a particle size distribution of 105–300 μm.

Formulation Example 28: (Fine Granular Formulation)

To a mixture of diatomaceous earth (Oplite P-1200, a product by Hokushu Keisoudo; 55 g) and carboxymethyl cellulose (Serogen 7A, a product by Dai-ichi Kogyo Seiyaku Co., Ltd.; 1.1 g) was added a suspension of conidia of *Exserohilum monoceras* B232 ($10^{10}$ conidia) in 400 mL of water and mixed with each other. Leodol SP-010 (a product by Kao Corporation; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (74.4 g) was blended with the above-prepared conidium suspension and further blended with white carbon (Carplex 80, a product by Shionogi & Co., Ltd.; 154 g). The resultant mixture was dried in air, and the dried mass was ground to obtain fine granules having a particle size distribution of 105–300 μm.

Formulation Example 29: (Fine Granular Formulation)

To a mixture of diatomaceous earth (Oplite P-1200, a product by Hokushu Keisoudo; 55 g) and carboxymethyl cellulose (Serogen 7A, a product by Dai-ichi Kogyo Seiyaku Co., Ltd.; 1.1 g) was added a suspension of conidia of *Exserohilum monoceras* B263 ($10^{10}$ conidia) in 400 mL of water and mixed with each other. Emasol O-10 (a product by Kao Corporation; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (74.4 g) was blended with the above-prepared conidium suspension and further blended with white carbon (Carplex 80, a product by Shionogi & Co., Ltd.; 154 g). The resultant mixture was dried in air, and the dried mass was ground to obtain fine granules having a particle size distribution of 105–300 μm.

Formulation Example 30: (Fine Granular Formulation)

To a mixture of diatomaceous earth (Oplite P-1200, a product by Hokushu Keisoudo; 55 g) and carboxymethyl cellulose (Serogen 7A, a product by Dai-ichi Kogyo Seiyaku Co., Ltd.; 1.1 g) was added a suspension of conidia of *Exserohilum monoceras* B276 ($10^{10}$ conidia) in 400 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (74.4 g) was blended with the above-prepared conidium suspension and further blended with white carbon (Carplex 80, a product by Shionogi & Co., Ltd.; 154 g). The resultant mixture was dried in air, and the dried mass was ground to obtain fine granules having a particle size distribution of 105–300 μm.

Formulation Example 31: (Fine Granular Formulation)

To a mixture of diatomaceous earth (Oplite P-1200, a product by Hokushu Keisoudo; 5 g) and carboxymethyl cellulose (Serogen 7A, a product by Dai-ichi Kogyo Seiyaku Co., Ltd.; 0.1 g) was added a suspension of conidia of *Curvularia sp.* B236 ($10^{10}$ conidia) in 40 mL of water and mixed with each other. Kadenax SO-80 (a product by Lion Corporation; 10.3%), castor oil (51.1%), lanolin (a product by Wako Pure Chemical Industries, Ltd.; 19.3%), paraffin wax (a product by Wako Pure Chemical Industries, Ltd.; 10.3%), a glycerol fatty acid ester (a product by Wako Pure Chemical Industries, Ltd.; 4.3%) and glycerol (a product by Wako Pure Chemical Industries, Ltd.; 4.3%) were mixed at 80° C. to obtain a homogeneous oil mixture. After cooling to room temperature, this oil mixture (40 g) was blended with the above-prepared conidium suspension and further blended with white carbon (Carplex 80, a product by Shionogi & Co., Ltd.; 48 g). The resultant mixture was dried in air, and the dried mass was ground to obtain fine granules having a particle size distribution of 105–300 μm.

Formulation Example 32: (Fine Granular Formulation)

To a mixture of diatomaceous earth (Oplite P-1200, a product by Hokushu Keisoudo; 5 g) and carboxymethyl cellulose (Serogen 7A, a product by Dai-ichi Kogyo Seiyaku Co., Ltd.; 0.1 g) was added a suspension of conidia of *Altenaria helianthi* IFO-9089 ($10^9$ conidia) in 40 mL of water and mixed with each other. Kadenax SO-80 (a product by Lion Corporation; 10.3%), castor oil (51.5%), lanolin (a product by Wako Pure Chemical Industries, Ltd.; 19.3%), paraffin wax (a product by Wako Pure Chemical Industries, Ltd.; 10.3%), a glycerol fatty acid ester a product by Wako Pure Chemical Industries, Ltd.; 4.3%) and glycerol (a product by Wako Pure Chemical Industries, Ltd.; 4.3%) were mixed at 80° C. to obtain a homogeneous oil mixture. After cooling to room temperature, this oil mixture (40 g) was blended with the above-prepared conidium suspension and further blended with white carbon (Carplex 80, a product by Shionogi & Co., Ltd.; 48 g). The resultant mixture was dried in air, and the dried mass was ground to obtain fine granules having a particle size distribution of 105–300 μm.

Formulation Example 33: (Fine Granular Formulation)

To a mixture of diatomaceous earth (Oplite P-1200, a product by Hokushu Keisoudo; 55 g) and carboxymethyl cellulose (Serogen 7A, a product by Dai-ichi Kogyo Seiyaku Co., Ltd.; 1.1 g) was added a suspension of conidia of *Nimbya scirpicola* K-004 ($10^9$ conidia) in 400 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.; 4%) were mixed at 80° C. to obtain a homogeneous oil mixture. After cooling to room temperature, this oil mixture (74.4 g) was blended with the above-prepared conidium suspension and further blended with white carbon (Carplex 80, a product by Shionogi & Co., Ltd.; 154 g). The resultant mixture was dried in air, and the dried mass was ground to obtain fine granules (470 g) having a particle size distribution of 105–300 μm.

Formulation Example 34: (Fine Granular Formulation)

To a mixture of diatomaceous earth (Radiorite 700, a product by Showa chemical Industry, Co., Ltd.; 55 g) and carboxymethyl cellulose (Serogen 7A, a product by Dai-ichi Kogyo Seiyaku Co., Ltd.; 1.1 g) was added a suspension of conidia of *Epiciccosorus nematosporus* K-035 ($10^{11}$ conidia) in 400 mL of water and mixed with each other. Hostaserin WOL (a product by Hoechst; 9.7%), light white oil (a product by Sigma; 48.4%), lanolin (a product by Wako Pure Chemical Industries, Ltd.; 24.2%), paraffin wax (a product by Wako Pure Chemical Industries, Ltd.; 9.7%), a glycerol fatty acid ester (a product by Wako Pure Chemical Industries, Ltd.; 4%) and glycerol (a product by Wako Pure Chemical Industries, Ltd.;, 4%) were mixed at 80° C. to obtain a homogeneous oil mixture. After cooling to room temperature, this oil mixture (74.4 g) was blended with the above-prepared conidium suspension and further blended with white carbon (Carplex 80, a product by Shionogi & Co., Ltd.; 154 g). The resultant mixture was dried in air, and the dried mass was ground to obtain fine granules having a particle size distribution of 105–300 μm.

The below-described comparative formulations were prepared according to the procedures described in the specifications of Japanese Patent Application Laid-open Nos. 4-226905, 4-360678 and 6-329513.

Comparative Formulation Example 1: (Granular Formulation)

Zeolite (a product by Wako Pure chemical Industries, Ltd.; 96%), sodium lignin sulfonate (SunEkis, a product by Nippon Paper Industries Co., Ltd.; 2%) and Neopelex (a product by Kao Corporation; 2%) were thoroughly mixed to obtain a powder mix (total 100%). The powder mix (13.6%) was mixed with a suspension of conidia of *Exserohilum monoceras* JTB-808 ($10^9$ conidia; 46.4%) in water (40 mL; 40%). The resultant mixture was dried in air, and the dried mass was ground to obtain granules having a particle size distribution of 0.3–3 mm.

Comparative Formulation Example 2: Wettable Powder

Neopelex (a product by Kao Corporation; 2% [regarding the total amount of an inactive ingredient as 100%]), Triton X-100 (a product by Wako Pure chemical Industries, Ltd.; 2%), white carbon (Carplex 80, a product by Shionogi & Co., Ltd.; 5%) and a suspension of conidia of *Exserohilum monoceras* JTB-808 ($10^9$ conidia) in 80 mL of water were mixed. The resultant mixture was dried in air, and then blended with diatomaceous earth (91%). The resultant was fully ground to obtain wettable powder.

Comparative Formulation Example 3: Floable Formulation

To a 10% sodium alkylbenzenesulfonate solution (SunEkis P252, a product by Nippon Paper Industries Co., Ltd.; 80mL) was suspended conidia of *Exserohilum monoceras* JTB-808 so that the population density of the conidia in the finished floable formulation became $10^9$ conidia/mL. To the resultant conidium suspension was dissolved a 4% xanthan gum solution (Keruzan S, a product by Keruko) (9.6 mL) to obtain a floable formulation.

Comparative Formulation Example 4: Capsule

Conidia of *Exserohilum monoceras* JTB-808 ($10^8$ conidia) was suspended in a mix solution (1 mL) comprising sodium alginate (a product by Wako Pure Chemical Industries, Ltd.; 0.7%), kaolin (a product by Wako Pure Chemical Industries, Ltd.; 5%) and glycerol (a product by Wako Pure Chemical Industries, Ltd.; 15%) in water (79.3%). The resultant suspension was dripped into a 0.2M solution of calcium acetate (a product by Wako Pure Chemical Industries, Ltd.) to prepare capsular products. The capsular products were cut into individual capsules, filtered and then dried in air to obtain capsule formulation.

Example 1

Long-Term Storage Test

The formulations prepared in by the above methods and a control solution (a conidium suspension) were stored at 4° C., and sampled at certain time intervals. About 0.1 g of each of the formulations was suspended into a 0.02% Tween-20 solution and inoculated on a pre-sterilized potato dextrose agar medium (a product by DIFCO). After cultivating in the dark at 25° C. for 15 hours, the culture medium was subjected to determination of germination percentage of spores. The germination percentage was determined by counting the population of germ spores in a randomly selected 100 spores under microscopic observation. This counting procedure was repeated five times and the numbers obtained were averaged to evaluate the long-term storage property of each formulation. The results are shown in Table 1.

TABLE 1

Long-term Stability

| Formulations | Germination percentage of spores (%) | | |
|---|---|---|---|
| | after 4 months | after 8 months | after 17 months |
| Formulation Ex. 1 (stored at 4° C.) | 98 | 96 | 82 |
| Formulation Ex. 2 (stored at 4° C.) | 99 | 85 | 77 |
| Com. Formulation Ex. 3 (stored at 4° C.) | 20 | 0 | 0 |
| Conidium suspension (stored at 4° C.) | 0 | — | — |

As shown in Table 1, it has become proven that the microbial pesticides of the invention are excellent in long-term storage stability.

Example 2

Test for Water Floating Property

The above-prepared formulations and comparative formulations were evaluated on their floating property on water.

Desalted water (300 mL) was pored into a 500 mL-beaker. 0.1 g of each of the formulations was dripped onto the center portion of the water surface in the beaker and was allowed to stand at room temperature, and the time required for sedimentation of all of the formulation was determined. In this test, a formulation sample which did not cause sedimentation even after 24 hours was judged to have a water floating property. The results are shown in Table 2.

TABLE 2

Water Floating Property

| Formulation | Time for sedimentation | Water floating property |
|---|---|---|
| Formulation Ex. 1 | >24 hours | floating |
| Formulation Ex. 2 | >24 hours | floating |
| Formulation Ex. 3 | >24 hours | floating |
| Formulation Ex. 4 | >24 hours | floating |
| Formulation Ex. 5 | >24 hours | floating |
| Formulation Ex. 6 | >24 hours | floating |
| Formulation Ex. 7 | >24 hours | floating |
| Formulation Ex. 8 | >24 hours | floating |
| Formulation Ex. 9 | >24 hours | floating |
| Formulation Ex. 10 | >24 hours | floating |
| Formulation Ex. 11 | >24 hours | floating |
| Formulation Ex. 12 | >24 hours | floating |
| Formulation Ex. 13 | >24 hours | floating |
| Formulation Ex. 14 | >24 hours | floating |
| Formulation Ex. 15 | >24 hours | floating |
| Formulation Ex. 16 | >24 hours | floating |
| Formulation Ex. 17 | >24 hours | floating |
| Formulation Ex. 18 (samples of all particle size distributions) | >24 hours | floating |
| Formulation Ex. 19 | >24 hours | floating |
| Formulation Ex. 20 | >24 hours | floating |

TABLE 2-continued

Water Floating Property

| Formulation | Time for sedimentation | Water floating property |
|---|---|---|
| Formulation Ex. 21 | >24 hours | floating |
| Formulation Ex. 22 | >24 hours | floating |
| Formulation Ex. 23 | >24 hours | floating |
| Formulation Ex. 24 | >24 hours | floating |
| Formulation Ex. 25 | >24 hours | floating |
| Formulation Ex. 26 | >24 hours | floating |
| Formulation Ex. 27 | >24 hours | floating |
| Formulation Ex. 28 | >24 hours | floating |
| Formulation Ex. 29 | >24 hours | floating |
| Formulation Ex. 30 | >24 hours | floating |
| Formulation Ex. 31 | >24 hours | floating |
| Formulation Ex. 32 | >24 hours | floating |
| Formulation Ex. 33 | >24 hours | floating |
| Formulation Ex. 34 | >24 hours | floating |
| Com. Formulation Ex. 1 | 10 sec. | no |
| Com. Formulation Ex. 2 (wettable powder) | 10 sec. | no |
| Com. Formulation Ex. 3 | >24 hours | floating |
| Com. Formulation Ex. 4 | 10 sec. | no |

Example 3

Test For Weed Controlling Effect of Formulations against *Echinochloa crus-galli*

Thirty-five of *Echinochloa crus-galli* seedlings were grown approximately to the 1-leaf stage in a pot of 1/10000-are containing soils from a paddy field, and 20 of the seedlings which grew in a same level were selected and left in the pot. The pot was flooded to keep the seedlings submarged. The pot was treated with each the formulations prepared in Formulation Examples 1–9, 23–31 and Comparative Formulation Examples 1–3. As control test solutions, each of a Triton 100-X solution with no conidium (no treatment) and a conidium suspension in a Triton X-100 solution were used to treat the pot. The treatment conditions are as follows.

No Treatment:

One mL of a 0.02% aqueous solution of Triton X-100 was applied to the pot dropwise (equivalent to 10 L/are).

Treatment With a Conidium Suspension:

A suspension of $1 \times 10^5$ conidia of *Exserohilum monoceras* JTB-808 (equivalent to to $1 \times 10^9$ conidia/are) in 1 mL of a 0.02% aqueous solution of Triton X-100 (equivalent to 10 L/are) was prepared and applied to the pot dropwise Treatment With Formulations:

Each of the above-mentioned formulations was applied to the pot so that the population of the microorganism conidia became $1 \times 10^5$ conidia/pot (equivalent to $1 \times 10^9$ conidia/are) After applying each of the above-mentioned application solution, the seedlings in the pot were allowed to grow for four weeks and observed their growth in the pot. The herbicidal activity was evaluated as follows: when there was no difference in growth of the seedlings between a treated pot and the untreated pot, the herbicidal activity of the treated pot was judged as "0%", whereas when all of the seedlings in a treated pot was dead, the herbicidal activity was judged as "100%". The results are shown in Table 3.

TABLE 3

Herbicidal effect of formulations

| Formulation | Herbicidal activity (%) |
|---|---|
| Formulation Ex. 1 | 100 |
| Formulation Ex. 2 | 100 |
| Formulation Ex. 3 | 100 |
| Formulation Ex. 4 | 100 |
| Formulation Ex. 5 | 100 |
| Formulation Ex. 6 | 100 |
| Formulation Ex. 7 | 100 |
| Formulation Ex. 8 | 100 |
| Formulation Ex. 9 | 100 |
| Formulation Ex. 23 | 100 |
| Formulation Ex. 24 | 100 |
| Formulation Ex. 25 | 100 |
| Formulation Ex. 26 | 100 |
| Formulation Ex. 27 | 100 |
| Formulation Ex. 28 | 100 |
| Formulation Ex. 29 | 100 |
| Formulation Ex. 30 | 100 |
| Formulation Ex. 31 | 100 |
| Com. Formulation Ex. 1 | 30 |
| Com. Formulation Ex. 2 | 30 |
| Com. Formulation Ex. 3 | 50 |
| Com. Formulation Ex. 4 | 20 |
| Conidium suspension | 98 |
| No treatment | 0 |

Example 4

Effect of Particle Size of Formulation on Herbicidal Activity Against *Echinochloa crus-galli*

Thirty-five of *Echinochloa crus-galli* seedlings were growin approximately to the 1-leaf stage in a pot of 1/10000-are containing soils from a paddy field, and 20 of the seedlings which grew in a same level were selected and left in the pot. The pot was flooded to keep the seedlings submarged. The pot was treated with each the formulations prepared in Formulation Example 18. As control test solutions, each of a Triton 100-X solution with no conidium (no treatment) and a conidium suspension in a Triton X-100 solution were used to treat the pot. The treatment conditions are as follows.

No Treatment:

One mL of a 0.02% aqueous solution of Triton X-100 was applied to the pot dropwise (equivalent to 10 L/are).

Treatment With a Conidium Suspension:

A suspension of $1 \times 10^5$ conidia of *Exserohilum monoceras* JTB-808 (equivalent to $1 \times 10^9$ conidia/are) in 1 mL of a 0.02% aqueous solution of Triton X-100 (equivalent to 10 L/are) was prepared and applied to the pot dropwise.

Treatment With Formulations:

Each of the above-mentioned formulations was applied to the pot so that the population of the microorganism conidium became $1 \times 10^5$ conidia/pot (equivalent to $1 \times 10^9$ conidia/are).

After applying each of the above-mentioned application solution, the seedlings in the pot were allowed to grow for four weeks and observed their growth in the pot. The herbicidal activity was evaluated as follows: when there was no difference in growth of the seedling between a treated pot and the untreated pot, the herbicidal activity in the treated pot was judged as "0%", whereas when all of the seedlings in a treated pot was dead, the herbicidal activity was judged as "100%". The results are shown in Table 4.

TABLE 4

Effect of particle size of formulation on herbicidal activity

| Formulation | Particle size distribution (μm) | Herbicidal activity (%) |
|---|---|---|
| Large granular formulation | 1700< | 58 |
| Granular formulation | 710–1700 | 70 |
| Small granular formulation | 300–710 | 77 |
| Fine granular formulation | 212–300 | 95 |
| Fine granular formulation | 106–212 | 93 |
| Fine granular formulation F | 63–106 | 96 |
| Powder formulation | 63> | 94 |
| Conidium suspension |  | 85 |
| No treatment |  | 0 |

As shown in Table 4, although all of the formulations floated on water and exhibited a herbicidal activity against *Echinochloa crus-galli*, the formulations having a smaller particle size distribution exhibited better dispersibility of the conidia into water and therefore showed higher herbicidal activity. From these results, it was found that formulations having a particle size distribution of not larger than 300 μm are preferable.

Example 5

Effect of Content of Conidium in Formulation on Herbicidal Activity Against *Echinochloa crus-galli*

Thirty-five of *Echinochloa crus-galli* seedlings were grown approximately to the 1-leaf stage in a pot of 1/10000-are containing soils from a paddy field, and 20 of the seedlings which grew in a same level were selected and left in the pot. The pot was flooded to keep the seedlings submarged. The pot was treated with each of the formulations prepared in Formulation Examples 19–21. As control test solutions, each of a Triton 100-X solution with no conidium (no treatment) and a conidium suspension in a Triton X-100 solution were used to treat the pot. The treatment conditions are as follows.

No Treatment:

One mL of a 0.02% aqueous solution of Triton X-100 was applied to the pot dropwise (equivalent to 10 L/are).

Treatment With a Conidium Suspension:

A suspension of $1 \times 10^4$ conidia of *Exserohilum monoceras* JTB-608 (equivalent to $1 \times 10^8$ conidia/are) in 1 mL of a 0.02% aqueous solution of Triton X-100 (equivalent to 10 L/are) was prepared and applied to the pot dropwise.

Treatment With Formulations:

Each of the above-mentioned formulations was applied to the pot so that the population of the conidium became $1 \times 10^4$ conidia/pot (equivalent to $1 \times 10^8$ conidia/are).

After applying each of the above-mentioned application solution, the seedlings in the pot were allowed to grow for four weeks and observed their growth in the pot. The herbicidal activity was evaluated as follows: when there was no difference in growth of the seedlings between a treated pot and the untreated pot, the herbicidal activity in the treated pot was judged as "0%", whereas when all of the seedlings in a treated pot was dead, the herbicidal activity was judged as "100%". The results are shown in Table 5.

TABLE 5

Effect of conidium content in formulation on herbicidal activity

| Formulation | Conidium content | Herbicidal activity (%) |
|---|---|---|
| Powder formulation | $1.77 \times 10^4$/g | 33 |
| Formulation Ex. 19 | $1.68 \times 10^4$/g | 40 |
| Formulation Ex. 20 | $3.99 \times 10^3$/g | 70 |
| Formulation Ex. 21 | $1.20 \times 10^3$/g | 60 |
| Conidium suspension | $1 \times 10^4$/mL | 33 |
| No treatment | | 0 |

Example 6

Effect of Oil Content in Formulation in Herbicidal Activity Against *Echinochloa crus-galli*

Thirty-five of *Echinochloa crus-galli* seedlings were grown approximately to the 1-leaf stage in a pot of 1/10000-are containing soils from a paddy field, and 20 of the seedlings which grew in a same level were selected and left in the pot. The pot was flooded to keep the seedlings submarged. The pot was treated with each of the formulations prepared in Formulation Examples 10–17. As control test solutions, each of a Triton 100-X solution with no conidium (no treatment) and a conidium suspension in a Triton X-100 solution were used to treat the pot. The treatment conditions are as follows.

No Treatment:

One mL of a 0.02% aqueous solution of Triton X-100 was applied to the pot dropwise (equivalent to 10 L/are).

Treatment With a Conidium Suspension:

A suspension of $1 \times 10^5$ conidia of *Exserohilum monoceras* JTB-808 (equivalent to $1 \times^9$ conidia/are) in 1 mL of a 0.02% aqueous solution of Triton X-100 (equivalent to 10 L/are) was prepared and applied to the pot dropwise.

Treatment With Formulations:

Each of the above-mentioned formulations having various oil contents was applied to the pot so that the population of the conidium became $1 \times 10^5$ conidia/pot (equivalent to $1 \times 10^9$ conidia/are).

After applying each of the above-mentioned application solution, the seedlings in the pot were allowed to grow for four weeks and observed their growth in the pot. The herbicidal activity was evaluated as follows: when there was no difference in growth of the seedlings between a treated pot and the untreated pot, the herbicidal activity in the treated pot was judged as "0%", whereas when all of the seedlings in a treated pot was dead, the herbicidal activity was judged as "100%". The results are shown in Table 6.

TABLE 6

Effect of oil content in formulation on herbicidal activity

| Formulation | Herbicidal activity (%) |
|---|---|
| Formulation Ex. 10 | 62 |
| Formulation Ex. 11 | 88 |
| Formulation Ex. 12 | 88 |
| Formulation Ex. 13 | 91 |
| Formulation Ex. 14 | 65 |
| Formulation Ex. 15 | 91 |
| Formulation Ex. 16 | 94 |
| Formulation Ex. 17 | 82 |

TABLE 6-continued

Effect of oil content in formulation on herbicidal activity

| Formulation | Herbicidal activity (%) |
|---|---|
| Conidium suspension | 97 |
| No treatment | 0 |

As shown in Table 6, significant difference was not observed in herbicidal activity among the formulations having various oil contents.

Example 7

Effect of Formulation on Various Crops

In this experiment, rice plant, wheat, eggplant, soybean, cabbage, cucumber and *Echinochloa crus-galli* were used as the plants to be tested. Seedlings of each of these plants were allowed to grow to the 2–5 leaf stage and provided as test plants.

A microbial pesticide of the invention was prepared according to the procedure as mentioned in Formulation Example 1 using conidia of *Exserohilum monoceras* JTB-808 strain which had been cultured in oatmeal sucrose agar medium. The resultant microbial pesticide was suspended in a 0.02% solution of Tween-20 in a concentration of $10^6$ conidia/mL and the resultant suspension was inoculated to the seedlings of each of the plants with an air spray. Just after the inoculation, the seedlings were allowed to stand in a moisture chamber which had been maintained at 25° C. and then transferred to a green house which had also been maintained at 25° C. After three weeks, the rate of diseased seedlings and the controlling rate were determined with respect to each of the plants. The results are shown in Table 7. With respect to *Echinochloa crus-galli*, the rate of diseased seedlings was 100%.

TABLE 7

| Effect on various crops | |
|---|---|
| Plant | Pathogenisity |
| Rice | − |
| Wheat | − |
| Eggplant | − |
| Soybean | − |
| Cabbage | − |
| Cucumber | − |
| *Echinochloa crus-galli* | + |

+: Death or inhibition to the growth
−: No effect

As shown in Table 7, the microbial pesticide of the present invention showed no herbicidal effect against rice plant, wheat, eggplant, soybean, cabbage and cucumber.

Example 8

Herbicidal Effect of Formulation Against *Echinochloa crus-galli* (Field Test)

A field was partitioned into 1/100-are sections using corrugated plastic sheeting, and rice plant was transplanted into each of the section and germinated *Echinochloa crus-galli* seedlings was also seeded thereinto. When the *Echinochloa crus-galli* was grown approximately to the 1-leaf stage, the section was flooded to keep the *Echinochloa crus-galli* underwater of 7 cm in water depth, and then treated with the formulation prepared in Formulation Example 22 in various application amount. As control test solutions, each of a Triton 100-X solution with no conidium (no treatment) and a conidium suspension in a Triton X-100 solution were used to treat the pot. The treatment conditions are as follows.

No Treatment:

One hundred mL of a 0.02% aqueous solution of Triton X-100 was applied to the section dropwise (equivalent to 10 L/are).

Application of Conidium Suspensions:

Two kinds of suspensions of conidium of *Exserohilum monoceras* JTB-808 in 100 mL of a 0.02% aqueous solution of Triton X-100 were prepared, which respectively contained $3\times10^7$ and $1\times10^8$ conidia. Each of these suspensions was applied to the section dropwise (equivalent to $3\times10^9$ conidia/are and $1\times10^{10}$ conidia/are, respectively).

Application of a Formulation:

The formulation prepared in Formulation Example 22 was applied to the field in such an amount that the conidium concentration in each section became $3\times10^7$ conidia or $1\times10^8$ conidia per section (equivalent to $3\times10^9$ conidia/are and $1\times10^1$ conidia/are), respectively.

After applying each of the above-mentioned application solution, the seedlings in the section were allowed to grow for four weeks, observed their growth, and counted the population of the seedlings remaining in the section to determine the controlling rate. Further, comprehensive controlling rate was evaluated as follows: when there was no difference in growth of the seedlings between a treated section and the untreated section, the comprehensive controlling rate in the test section was judged as "0%", whereas when all of the seedlings in a treated section was dead, the comprehensive controlling rate was judged as "100%". The results are shown in Table 8.

TABLE 8

Herbicidal effect of formulations against *Echinochloa crus-galli*

| | | Herbicidal activity (%) | |
|---|---|---|---|
| Formulation | Amount treated | Controlling rate based on population of plant* | Comprehensive Controlling rate** |
| Forml. Ex. 22 | 2 kg ($3 \times 10^{10}$/10a) | 96 | 96 |
| Forml. Ex. 22 | 6 kg ($1 \times 10^{11}$/10a) | 100 | 100 |
| Conidium suspension | ($3 \times 10^{10}$/10a) | 99 | 100 |
| Conidium suspension | ($1 \times 10^{11}$/10a) | 100 | 100 |
| No treatment | | 0 | 0 |

*Controlling rate based on population of plants = (1 – remaining population of *Echinochloa crus-galli* in treated section/remaining population of *Echinochloa crus-galli* in untreated section) × 100; and
**Comprehensive controlling rate: overall reduction rate of *Echinochloa crus-galli*

As shown in Table 8, the microbial pesticides of the invention exhibited excellent controlling effect against *Echinochloa crus-galli* but exhibited no effect against rice plant.

What is claimed is:

1. A water-floating microbial pesticide comprising a microorganism, a water-in-oil surfactant, oil, and powder having a low bulk specific gravity.

2. The water-floating microbial pesticide containing a microorganism according to claim 1, wherein the microorganism has herbicidal activities.

3. The water-floating microbial pesticide according to claim 2, wherein the microorganism belongs to the genus Exserohilum.

4. The water-floating microbial pesticide according to claim 3, wherein the microorganism belonging to the genus Exserohilum is *Exserohilum monoceras*.

5. The water-floating microbial pesticide according to any one of claims 1 to 4, wherein the water-in-oil surfactant has an HLB value within the range of 3 to 7.

6. The water-floating microbial pesticide according to claim 5, wherein the water-in-oil surfactant is a nonionic surfactant selected from the group consisting of polyglyceryl stearate type, sorbitan stearate type, polyglyceryl oleate type, sorbitan oleate type, monoglycerin ester type, sorbitan ester type, glycerol fatty acid ester type and nonyl phenol type ones.

7. The water-floating microbial pesticide according to claim 1 wherein the powder having a low bulk specific gravity is white carbon.

8. A method for producing a water-floating microbial pesticide, which comprises suspending a microorganism in water, adding oil containing a water-in-oil surfactant to the resultant suspension and mixing with each other, and adding powder having a low bulk specific gravity to the resultant mixture to obtain the microbial pesticide.

9. The method according to claim 8, wherein the suspension further comprises a mineral carrier suspended therein.

10. A method for using the water-floating microbial pesticide according to claim 1 which comprises applying the water-floating microbial pesticide to a paddy filed.

11. The method according to claim 10, for controlling plants belonging to the genus Echinochloa.

12. A water-floating microbial pesticide formulation, comprising:

an effective pesticidal amount of a microorganism;

a water-in-oil surfactant;

oil formulation; and a powder having a bulk specific gravity of not more than 1.

13. The water-floating microbial pesticide formulation according to claim 12, wherein said microorganism is a fungi which has conidia having a hydrophobic surface.

14. The water-floating microbial pesticide formulation according to claim 12, wherein said microorganism is a fungi used in the form of conidia.

15. The water-floating microbial pesticide formulation according to claim 12, wherein said microorganism is a fungi used in the form of myclium.

16. The water-floating microbial pesticide formulation according to claim 14, wherein conidia of *Exserohilum monoceras* is present in an amount of $1\times10^3$ to $1\times10^9$ conidia per gram.

17. The water-floating microbial pesticide formulation according to claim 13, wherein said surfactant is present in an amount of 0.1 to 10% by weight based on the total weight of the formulation;

said oil is present in an amount of 10 to 70% by weight based on the total weight of the formulation; and said powder is present in an amount of 10 to 80% by weight based on the total weight of the formulation.

18. The water-floating microbial pesticide formulation according to claim 13, wherein said surfactant is present in an amount of 1 to 5% by weight based on the total weight of the formulation;

said oil is present in an amount of 10 to 50% by weight based on the total weight of the formulation; and said powder is present in an amount of 30 to 60% by weight based on the total weight of the formulation.

* * * * *